(12) United States Patent
Hirao et al.

(10) Patent No.: US 6,811,753 B2
(45) Date of Patent: Nov. 2, 2004

(54) BLOOD TESTING TOOL

(75) Inventors: Konomu Hirao, Kyoto (JP); Yuichiro Noda, Kyoto (JP); Yoshiyuki Tanaka, Kyoto (JP); Takatoshi Uchigaki, Kyoto (JP)

(73) Assignee: Arkray, Inc., Kyoto (JP)

( * ) Notice: Subject to any disclaimer, the term of this patent is extended or adjusted under 35 U.S.C. 154(b) by 278 days.

(21) Appl. No.: 09/748,435

(22) Filed: Dec. 27, 2000

(65) Prior Publication Data

US 2001/0005488 A1 Jun. 28, 2001

(30) Foreign Application Priority Data

| Dec. 28, 1999 | (JP) | .......................................... 11-374825 |
| Mar. 24, 2000 | (JP) | ..................................... 2000-084352 |
| Mar. 24, 2000 | (JP) | ..................................... 2000-084353 |

(51) Int. Cl.[7] .............................................. G01N 33/48
(52) U.S. Cl. .......................... 422/101; 422/58; 422/61; 436/180
(58) Field of Search .............................. 422/56, 58, 61, 422/101; 436/68, 164, 166, 169; 438/180

(56) References Cited

U.S. PATENT DOCUMENTS

| 4,477,575 A | 10/1984 | Vogel |
| 4,816,224 A | 3/1989 | Vogel et al. |
| 5,064,541 A | 11/1991 | Jeng et al. |
| 5,846,837 A | 12/1998 | Thym et al. |
| 5,916,521 A | 6/1999 | Bunce et al. |
| 5,962,215 A | 10/1999 | Douglas et al. |

FOREIGN PATENT DOCUMENTS

| JP | 1-158350 A | 6/1989 |
| JP | 7-55809 A | 3/1995 |
| JP | 10-104226 | 4/1998 |

*Primary Examiner*—Lyle A. Alexander
(74) *Attorney, Agent, or Firm*—Merchant & Gould P.C.

(57) ABSTRACT

A blood testing tool is provided, which separates blood cells and can collect blood plasma or blood serum with a high yield. The blood testing tool includes an asymmetric porous membrane with a pore size distribution in which an average pore size varies to be reduced continuously or discontinuously in a thickness direction. The porous membrane includes a blood supply portion, a development portion, and a blood-cell blocking portion formed between the blood supply portion and the development portion and pores in the blood cell blocking portion include only pores through which blood cells cannot pass. When blood is supplied to one side with larger pores of the blood supply portion, the blood moves in a direction parallel to a surface of the porous membrane by a capillary phenomenon, but only blood plasma or blood serum moves into the development portion to develop.

26 Claims, 15 Drawing Sheets

BLOOD TESTING TOOL

BACKGROUND OF THE INVENTION

1. Field of the Invention

The present invention relates generally to a blood testing tool used for a blood test.

2. Related Background Art

In a blood test, a sheet blood testing tool consumed per specimen is used for various purposes. Examples of this testing tool include those that retain blood, from which blood to be tested is extracted; and those that are pre-impregnated with a reagent or the like so that the blood and the reagent react with each other with the result being measured by an optical or electrochemical method, etc.

Such a blood testing tool has been used for various purposes in general clinical tests or the like. In addition, the suitability of such a blood testing tool has been studied for use in remote clinical testing systems. Indeed it is actually used in certain remote clinical testing systems. In such a remote clinical testing system, a patient collects blood by himself at home, and the blood testing tool is impregnated with the blood. This is then dried, and the blood testing tool is then mailed to a test institute such as a hospital for testing. The patient who mailed the blood can then be informed of the test result by a mail or by visiting the hospital.

When the test item is a component of blood plasma or blood serum such as blood glucose or the like, blood cells must be separated in the blood testing tool. Generally, in a conventional blood testing tool, a blood cell separator such as a glass filter or the like is incorporated into the blood testing tool. However, a blood testing tool having an asymmetric porous membrane with pores whose sizes vary in a thickness direction has been developed recently. When blood is supplied to the porous membrane from the side having larger pores, blood cells are separated. The blood penetrates in the thickness direction and thus blood plasma or blood serum comes out of the other side. An advantage of using a blood testing tool having a porous membrane is that the clogging of blood cells can be prevented.

However, such conventional blood testing tools have the disadvantage that only a small amount of blood plasma or blood serum can be collected. For instance, a collection rate of blood plasma or blood serum in conventional blood testing tools is about 25% at most. Therefore, when a trace component in the blood plasma or blood serum is to be analyzed, there is the possibility that the trace component cannot be analyzed correctly due to the small size of the sample obtained. Particularly, in the case of the remote clinical testing system, where a patient collects blood himself, there is the difficulty of obtaining a large enough blood sample. In addition, since there are many test items, an increased amount of blood plasma or blood serum must be collected.

SUMMARY OF THE INVENTION

The present invention at least in its preferred embodiments is intended to provide a blood testing tool that can separate blood cells easily and can collect blood plasma or blood serum with a high yield.

In order to achieve the above-mentioned object, a blood testing tool includes an asymmetric porous membrane with a pore size distribution in which an average pore size varies so that it is reduced continuously or discontinuously in a thickness direction, wherein the asymmetric porous membrane includes a blood supply portion, a development portion, and a blood-cell blocking portion formed between the blood supply portion and the development portion, pores in the blood-cell blocking portion include only pores through which blood cells cannot pass, the arrangement being such that when blood is supplied to the blood supply portion at a side having larger pores, the blood moves in a direction substantially parallel to a surface of the asymmetric porous membrane by capillary action, but only blood plasma or blood serum moves into the development portion.

As described above, the blood testing tool of the present invention allows blood to move in the porous membrane in the direction parallel to the surface (a transverse direction) and blood cells can be separated during the movement. This is different from the conventional case where blood moves in a thickness direction and can induce a strong capillary action. Thus a large amount of blood plasma or blood serum can be collected. In addition, a sufficient region for retaining blood plasma or blood serum reaching the region can be secured. According to the preferred form of the blood testing tool of the present invention, therefore, blood plasma or blood serum can be obtained with an excellent collection rate and blood cells also can be separated adequately. In the blood testing tool, the collection rate of blood plasma or blood serum may be, for example, about 60 to 70%. In the blood testing tool, since the blood supply portion and the development portion do not lie one on top of another, measurement can be carried out from any sides of the development portion, when the measurement is to be carried out directly with respect to the blood testing tool by an optical method (including visual observation). In the present invention, the "pores through which blood cells cannot pass" are not limited to the pores with smaller sizes than spherical diameters of blood cells, but may be pores through which blood cells eventually cannot pass regardless of the mechanism of preventing blood cells from passing through the pores. Therefore, the pores through which blood cells cannot pass may include pores larger than the spherical diameters of blood cells. In addition, the "average pore size varies so that it is reduced discontinuously" means that the average pore size may vary, for example, to be reduced in a stepwise manner.

Preferably, the blood testing tool further includes a groove formed between the blood supply portion and the development portion, wherein a portion between a bottom of the groove and a part of a surface of the asymmetric porous membrane corresponding to the bottom is the blood-cell blocking portion.

The groove may be formed by compression or cutting out of a part of the asymmetric porous membrane.

Preferably, pores in the development portion include only pores through which blood cells cannot pass. In this case, the development portion also may function as the blood-cell blocking portion.

Preferably, the pores in the blood-cell blocking portion have a pore size in a range of 1 to 50 $\mu$m, more preferably 5 to 30 $\mu$m, and particularly preferably 10 to 20 $\mu$m.

It also is preferable that in the asymmetric porous membrane, the maximum pore size is in a range of 30 to 300 $\mu$m and the minimum pore size is in a range of 1 to 30 $\mu$m.

Preferably, the asymmetric porous membrane has a single layer structure. The single layer structure preferably includes no interface (i.e. no contact surface between layers). Therefore, blood plasma or blood serum can move more easily than if an interface were present, and hemolysis or the like caused by contact between blood cells and an interface can be prevented.

Preferably, the asymmetric porous membrane is supported by a supporter. Accordingly, regardless of the strength of the porous membrane, a blood testing tool with a sufficient strength can be obtained, which enables easy handling.

Preferably, the asymmetric porous membrane is formed from at least one resin selected from polysulfone, polyamide, polyimide, polycarbonate, polystyrene, polyaryl hydrazide, and the like. More preferably, the porous membrane is formed of polysulfone.

Furthermore, it is preferable that the asymmetric porous membrane is treated to be provided with hydrophilicity. This allows blood to develop easily in the porous membrane.

Preferably, the development portion contains a stabilizing agent for maintaining stability of components in the blood plasma or the blood serum.

Preferably, the development portion contains an analytical reagent. Accordingly, blood plasma or blood serum separated in the blood testing tool is allowed to react with the analytical reagent without being collected from the blood testing tool, thus analysis may be conducted.

The blood testing tool of the present invention may further include a holder, and the porous membrane may be contained in the holder. Examples of such a blood testing tool (hereinafter, referred to as a "contained-type blood testing tool") include, for instance, the following two forms.

In one such example there is a contained-type blood testing tool as discussed above further including a holder, wherein the holder contains the asymmetric porous membrane and a space with a size preventing a capillary phenomenon from occurring is formed between an inner wall of the holder and a portion between the development portion and the blood supply portion.

In a conventional blood testing tool with an asymmetric porous membrane contained in a holder, blood might penetrate not into the porous membrane but between the porous membrane and the inner wall of the holder in some cases. The blood thus penetrated is not separated by a chromatography effect. Therefore, blood components separated inside the porous membrane may be contaminated with the unseparated blood that has penetrated as described above, which may affect analysis. As a means for solving this problem, consideration can be given to a method of providing a sufficiently large development portion in the porous membrane. However, this makes the blood testing tool too big and costly, and inconvenient to use. Considering this, the present inventors studied the blood penetration between the porous membrane and the inner wall of the holder and found that it was caused by a capillary phenomenon occurring between the inner wall of the holder and the porous membrane. In the example of a contained-type blood testing tool in the present invention, therefore, blood cells can be separated adequately and an excellent collection rate can be achieved as described above. In addition, a space with a size not allowing this capillary phenomenon to occur is provided between the inner wall and the portion (hereinafter, also referred to as a "boundary portion") between the development portion and the blood supply portion of the porous membrane, thus preventing unseparated blood from penetrating therebetween.

In the porous membrane contained in the contained-type blood testing tool, with respect to the flow of blood inside the porous membrane, the blood supply portion denotes a part or the whole part of the portion upstream from the boundary portion, and the development portion denotes a part or the whole part of the portion downstream from the boundary portion.

Preferably, the portion between the blood supply portion and the development portion is the blood-cell blocking portion.

Preferably, a protruding supporter is formed inside the holder, wherein the protruding supporter lifts the portion between the development portion and the blood supply portion, thus forming the space. It also is preferable that a protruding holding portion is formed inside the holder on an opposite side to the side on which the protruding supporter is formed, wherein holding portion fixes the development portion to the inner wall of the holder on the side on which the protruding supporter is formed. Accordingly, the whole porous membrane also can be fixed stably.

The space is not particularly limited as long as its size prevents the capillary phenomenon from occurring and is determined suitably according to conditions such as blood viscosity (or surface tension), materials of the inner wall of the holder and the porous membrane, or the like. The space has a height of at least 0.05 mm, preferably in the range of 0.05 to 3 mm, more preferably 0.2 to 2 mm, and particularly preferably 0.3 to 0.7 mm.

In the contained-type blood testing tool, the size of the porous membrane may be determined according to the size of the inner portion of the holder. When the porous membrane has a rectangular shape, its size is, for example, in the range of 22×22 to 2×250 mm, preferably 20×25 to 3×167 mm, and more preferably 5×100 mm. The thickness of the porous membrane and the pore size are described later.

Materials for the holder may include, for example, polyethylene terephthalate (PET), polyvinyl chloride (PVC), acrylonitrile butadiene styrene copolymer (ABS), polypropylene (PP), acrylic resin, styrene, or the like. Preferably, the material of the holder is PET, ABS resin, and PP, more preferably PET and ABS resin. It also is preferable that a part of a portion of the holder corresponding to the development portion is transparent. When the part is transparent, the development of blood can be checked visually from the outside. Furthermore, the transparent portion is not limited to a part of the portion, thus the whole portion may be transparent. Examples of transparent material include acrylic resin, PET, PVC, ABS resin, or the like. Preferably, the transparent material is PET, PVC, or acrylic resin, and more preferably PET or PVC. For the same reason, a slit is preferably formed in a portion of the holder corresponding to the development portion.

In another example of a form of tool there is provided a contained-type blood testing tool further including a holder, wherein the holder contains the asymmetric porous membrane, the holder has a blood guide hole at a position corresponding to the blood supply portion, a predetermined space is provided between a lower end of the blood guide hole and the blood supply portion, and blood is retained in the space quantitatively by surface tension of the blood.

Conventionally, in a blood testing tool, quantitative analysis may be required in some cases and in such a case, it is necessary to supply a predetermined amount of blood to the blood testing tool. For instance, there is a method in which blood is collected quantitatively using a pipette or the like, which then is supplied to the blood testing tool. In another method, a blood testing tool is provided with quantitativity by the use of a capillary tube with a predetermined volume instead of an asymmetric porous membrane. In a further method, a blood testing tool is employed in which a porous membrane having quantitativity is used and blood is supplied to a particular area of the porous membrane.

However, the above method of supplying blood quantitatively using a pipette is complicated and is not practical in clinical tests requiring large amounts of blood to be treated. In the blood testing tool using the capillary tube, besides the capillary tube, an analyzor or the like is required and thus the configuration of the blood testing tool is complicated. Therefore, it is difficult to apply such a blood testing tool to multi-item tests. Such a complex configuration also makes the operation of collecting blood from the blood testing tool complicated. In addition, a porous membrane having quantitativity is expensive and therefore the use of this increases the cost of the blood testing tool. Generally, a porous membrane used in a blood testing tool is required to have various functions such as a filtration function, a function preventing effects on a reaction field, or the like. However, it is difficult to provide functions other than the quantitativity additionally for a porous membrane having quantitativity. Furthermore, a porous membrane having quantitativity tends to be affected easily by the nature of a specimen such as blood hematocrit, viscosity, or the like, therefore, it is difficult to maintain a specimen with variation in nature quantitatively. Moreover, in a conventional blood testing tool, there also is the problem that a specimen may penetrate the region between the porous membrane and the inner wall of the holder as described above, which affects the test.

According to the contained-type blood testing tool, however, the surface tension of blood may be utilized and therefore, as described above, not only can blood cells be separated adequately and an excellent collection rate be achieved, but also blood can be collected quantitatively with ease, at low cost, and with a simple configuration. In addition, since a predetermined space is provided between the lower end of the blood guide hole and the porous membrane, blood may be prevented from penetrating between the porous membrane and the inner wall of the holder. This is because no capillary phenomenon occurs due to the predetermined space in this case, since the blood penetration is caused by the capillary phenomenon.

The space has a height in the range of, for instance, 10 to 3000 μm, preferably 50 to 1500 μm, and more preferably 100 to 1000 μm.

Preferably, the holder has a hole and an annular protrusion is formed on an inner wall of the holder so as to surround the hole, so that the blood guide hole is formed by the hole and a space inside the annular protrusion, and an end of the annular protrusion is the lower end of the blood guide hole. Such an annular protrusion serves as a guide for guiding blood to the blood supply portion of the porous membrane.

Preferably, the part of the holder corresponding to the development portion is transparent or a slit is formed in the portion as described above.

The size of the porous membrane can be determined suitably according to, for example, the size of the holder in which the porous membrane is to be contained. In the case of using a strip-shaped porous membrane, for example, it may have a length of 1 to 300 mm and a width of 1 to 100 mm, preferably a length of 5 to 100 mm and a width of 5 to 50 mm, and more preferably a length of 10 to 50 mm and a width of 5 to 20 mm. The thickness of the porous membrane and the pore size are described later.

A contained-type blood testing tool according to the present invention may have both the configurations of the above-mentioned two contained-type blood testing tools. In other words, in a third contained-type blood testing tool having such configurations, preferably, the porous membrane is contained in a holder, wherein a space with a size preventing a capillary phenomenon from occurring is formed between an inner wall of the holder and a portion between the development portion and the blood supply portion. The holder has a blood guide hole at a position corresponding to the blood supply portion of the porous membrane, a predetermined space is provided between a lower end of the blood guide hole and the blood supply portion, and blood is retained in the space quantitatively by surface tension of the blood. In this contained-type blood testing tool, details of the respective parts are the same as described above.

Preferably, in the holder used for the contained-type blood testing tool, a protruding supporter is provided inside the holder for forming a space with a size preventing the capillary phenomenon from occurring by lifting a portion between the development portion and the supply portion of the porous membrane. In addition, for the same reason as described above, preferably, a protruding holding portion is formed for fixing the porous membrane to the inner wall of the holder, in an inner portion of the holder on an opposite side to the side where the supporter is provided. Moreover, preferably, a part of the portion of the holder corresponding to the development portion of the porous membrane is transparent or a slit is formed in the portion.

The size of the holder is not particularly limited. For example, the overall size may be 5 mm×30 mm to 50 mm×80 mm, the overall thickness may be 0.5 to 10 mm, the height of the protruding supporter may be 0.05 to 3.0 mm, and the height of the protruding holding portion may be 0.1 to 5.0 mm. Preferably, the overall size is 5 mm×40 mm to 40 mm×70 mm, the overall thickness is 0.5 to 5.0 mm, the height of the protruding supporter is 0.2 to 1.0 mm, and the height of the protruding holding portion is 0.3 to 2.0 mm. More preferably, the overall size is 10 mm×50 mm to 30 mm×60 mm, the overall thickness is 1.0 to 3.0 mm, the height of the protruding supporter is 0.3 to 0.7 mm, and the height of the protruding holding portion is 0.4 to 1.0 mm.

BRIEF DESCRIPTION OF THE DRAWINGS

FIGS. 1A and 1B show an example of a blood testing tool according to the present invention, wherein FIG. 1A is its plan view and FIG. 1B its sectional view.

FIGS. 5A, 5B, and 5C show yet another example of a blood testing tool according to the present invention, wherein FIG. 5A is its plan view, FIG. 5B its back face view, and FIG. 5C its sectional view.

FIGS. 7A, 7B, 7C, and 7D show a further example of a blood testing tool according to the present invention, wherein FIG. 7A is its plan view, FIGS. 7B and 7C are its sectional views, and FIG. 7D is its perspective view.

DETAILED DESCRIPTION OF THE INVENTION

Embodiment A-1

Figure 1A:
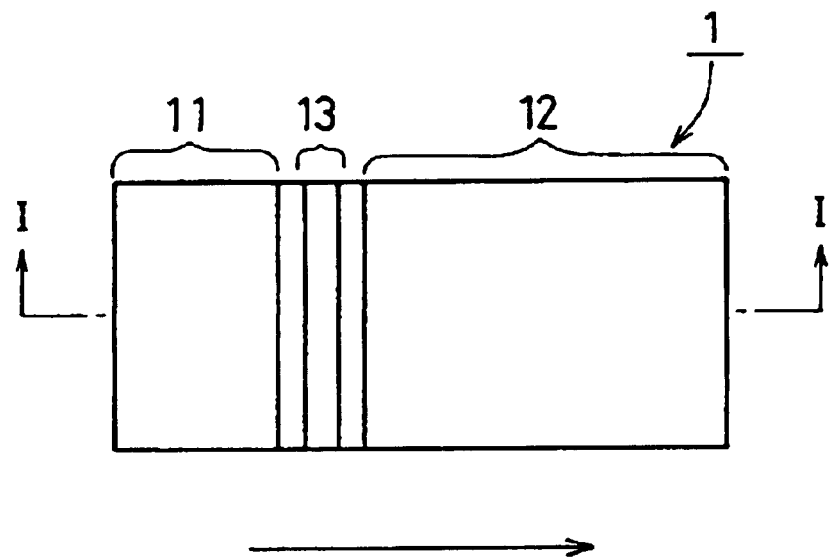
Figure 1B:
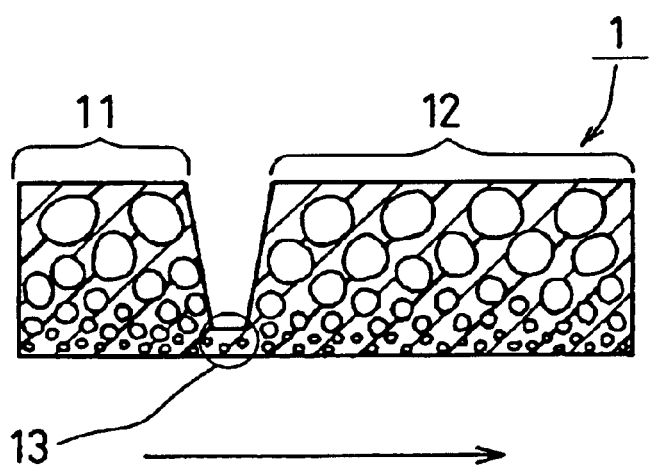

FIGS. 1A and 1B show an example of a blood testing tool according to the present invention. FIG. 1A is a plan view of the blood testing tool and FIG. 1B is a sectional view taken in the direction I—I shown in FIG. 1A. As shown in the figures, this blood testing tool 1 is formed of an asymmetric porous membrane with a single layer and includes a blood supply portion 11, a development portion 12, and a groove formed between them. A portion 13 between the bottom of the groove and a portion of the porous membrane surface corresponding to the bottom serves as a blood-cell blocking portion.

Examples of pore sizes in respective portions of the porous membrane are as follows. In the blood supply portion 11, the maximum pore size is, for example, in the range of 30 to 300 μm, preferably 50 to 150 μm, and the minimum pore size is, for example, in the range of 1 to 30 μm, preferably 5 to 10 μm. In the development portion 12, the maximum pore size is, for example, in the range of 30 to 300 μm, preferably 50 to 150 μm, and the minimum pore size is, for example, in the range of 1 to 30 μm, preferably 5 to 10 μm. In the blood-cell blocking portion 13, the pore size is, for example, in the range of 1 to 50 μm, preferably 5 to 30 μm.

The size of the porous membrane in the blood testing tool 1 is not particularly limited and can be determined according to the amount of a blood specimen to be supplied or the like. When the whole blood to be supplied is about 80 to 120 μl, preferably, the blood supply portion 11 has a thickness in the range of 50 to 500 μm, more preferably 150 to 400 μm, a length in the range of 1 to 30 mm, more preferably 5 to 15 mm, and a width in the range of 1 to 30 mm, more preferably 5 to 20 mm. Preferably, the development portion 12 has a thickness in the range of 50 to 500 μm, more preferably 150 to 400 μm, a length in the range of 1 to 50 mm, more preferably 10 to 40 mm, and a width in the range of 1 to 50 mm, more preferably 10 to 40 mm. Preferably, the blood-cell blocking portion 13 has a thickness in the range of 1 to 200 μm, more preferably 50 to 150 μm, a length in the range of 1 to 30 mm, more preferably 5 to 15 mm, and a width in the range of 1 to 2000 μm, more preferably 100 to 1000 μm. In addition, with respect to the groove, preferably, the width is in the range of 1 to 2000 μm, more preferably 100 to 1000 μm. Preferably, the blood testing tool 1 as a whole has a thickness in the range of 50 to 500 μm, more preferably 150 to 400 μm, an overall length in the range of 2 to 100 mm, more preferably 20 to 80 mm, and a width in the range of 1 to 50 mm, more preferably 10 to 40 mm.

It is preferred to form the porous membrane using such resins as described above. However, polysulfone is preferable due to its ease of manufacture and its stiffness. Such an asymmetric porous membrane may be produced using the resin. Alternatively, a commercially available asymmetric porous membrane, for example, BST-SP manufactured by U.S. Filter Corporation, MPS manufactured by Primecare, or the like may be used.

As described above, the porous membrane may be treated so as to be provided with a hydrophilicity by being dipped in a treatment solution such as, for example, hydrophilic polymers such as hydroxypropylcellulose (HPC), polyvinyl alcohol (PVA), carboxymethylcellulose (CMC), or the like, lecithin, a surfactant, or the like. The concentration of the treatment solution is, for example, in the range of 0.1 to 50 wt %, and the treatment time is, for instance, in the range of 0.1 to 24 hours. As a solvent of the solution, for example, water, various organic solvents, or the like can be used. The organic solvents include alcohols such as ethanol or the like.

In order to maintain the stability of components in blood plasma or blood serum to be developed and retained, as described above, the development portion 12 may contain a stabilizing agent, for example, saccharides such as sucrose, trehalose, lactose, glucose, or the like, salts such as sodium chloride, potassium chloride, or the like, buffers such as glycine, a phosphate buffer, a citrate buffer, or a Good's buffer, or the like. The content of the stabilizing agent can be determined suitably according to its kind or the like, but is, for instance, in the range of 0.01 to 100 mg per cubic centimeter of the development portion 12. One kind of stabilizing agent may be used, or two or more kinds may be used together. The stabilizing agent may be provided not only in the development portion 12 but also the whole porous membrane.

The groove can be formed, for example, by compression of a part of the surface of the porous membrane. For instance, the groove can be formed by compression through rolling of a disk-shaped roller or by compression using a cutting tool with a dull edge to a degree causing no cut. When the groove is formed by compression, the blood-cell blocking portion may include large pores in the porous membrane, but since the pores are deformed or crushed after compression, the blood cells are thus prevented from passing through the blood-cell blocking portion.

Alternatively, the groove may be formed, for example, by cutting off a part of the porous membrane using a cutting tool such as a cutter or the like. In this case, the size of the groove are the same as in the case described above.

Next, an example of preparing a blood plasma sample or a blood serum sample by adding blood to the blood testing tool 1 is described based on FIGS. 1A and 1B.

Initially, blood is dropped on the surface (the upper surface in FIG. 1B) of the blood supply portion 11 with larger pores. While the blood moves in the thickness direction inside the blood supply portion 11 and blood cells are separated, the blood moves in a direction (in the direction indicated with an arrow in FIG. 1B) parallel to the surface (hereinafter also referred to simply as a "surface direction"). In the blood that has moved in the surface direction to reach the blood blocking portion 13, blood cells cannot pass through the blood-cell blocking portion 13 and are captured, therefore only blood plasma or blood serum passes through the blood blocking portion 13 to be developed in the development portion 12.

After this, blood testing tool 1 is dried by forced air drying, natural air drying, or the like, then the development portion 12 is cut out from the blood testing tool 1, or the development portion 12 is subjected to punching or the like using a punch or the like.

A cut piece obtained by cutting or the like is put, for example, in a test tube and an extractant is added thereto, which then is left, thus extracting and collecting blood plasma or blood serum. The extractant is not particularly limited as long as it can extract blood plasma or blood serum and does not affect the detection of analytical target components in the blood plasma or blood serum. As the extractant, for example, a buffer solution, a physiological salt solution, purified water, a protein solution, or the like or a mixture thereof may be used. Examples of the buffer solution include various buffer solutions including phosphoric acid, citric acid, hydrochloric acid, acetic acid, or the like, and the pH of the buffer solution is, for example, in the range of 6 to 8. The amount of the extractant to be added is not particularly limited and can be determined according to the size of the cut piece or the like. The amount is, for example, 1 to 1000 times the volume of the cut piece. In addition, the time for an extracting process is not particularly limited and is, for example, in the range of 1 to 300 minutes.

Using the collection solution, the analytical target components in the blood plasma or blood serum are measured, and the amounts of the components thus determined.

Alternatively, it is also possible to analyze the blood plasma or blood serum retained in the development portion 12 in this blood testing tool 1 without collecting it using the extractant.

To this end, an analytical reagent may be provided in the development portion 12 beforehand. Then, the analytical reagent and components in developed blood plasma or blood serum react together in the development portion 12. This reaction is detected by an optical method, an electrochemical method, or the like, thus the analysis may be conducted easily.

Examples of the method for providing the reagent in the development portion include a printing method, an impregnation method, a spraying method, an application method, or the like. A solution of the reagent may be prepared, with which the development portion is impregnated by application, dipping, or the like, this is then dried, thus providing the reagent in the development portion.

The analytical reagent is not limited and can be determined according to the kind of a target component to be analyzed. Components of the reagent include, for example, various enzymes, buffer materials such as phosphate, carbonate, or the like, color couplers, or the like. When the target component is saccharide, for example, glucose oxidase (GOD), 4-aminoantipyrine, or the like can be used. Specifically, when the target component is glucose, for instance, glucokinase, glucose-6-phosphate dehydrogenase, β-NADP, ATP, a buffer solution, and the like may be provided. Furthermore, when the target component is albumin (Alb), for example, BCG (bromocresol green) can be used, and when the target component is total bilirubin (T-Bil), for instance, sulfanilic acid and nitrous acid can be used.

Figure 2:
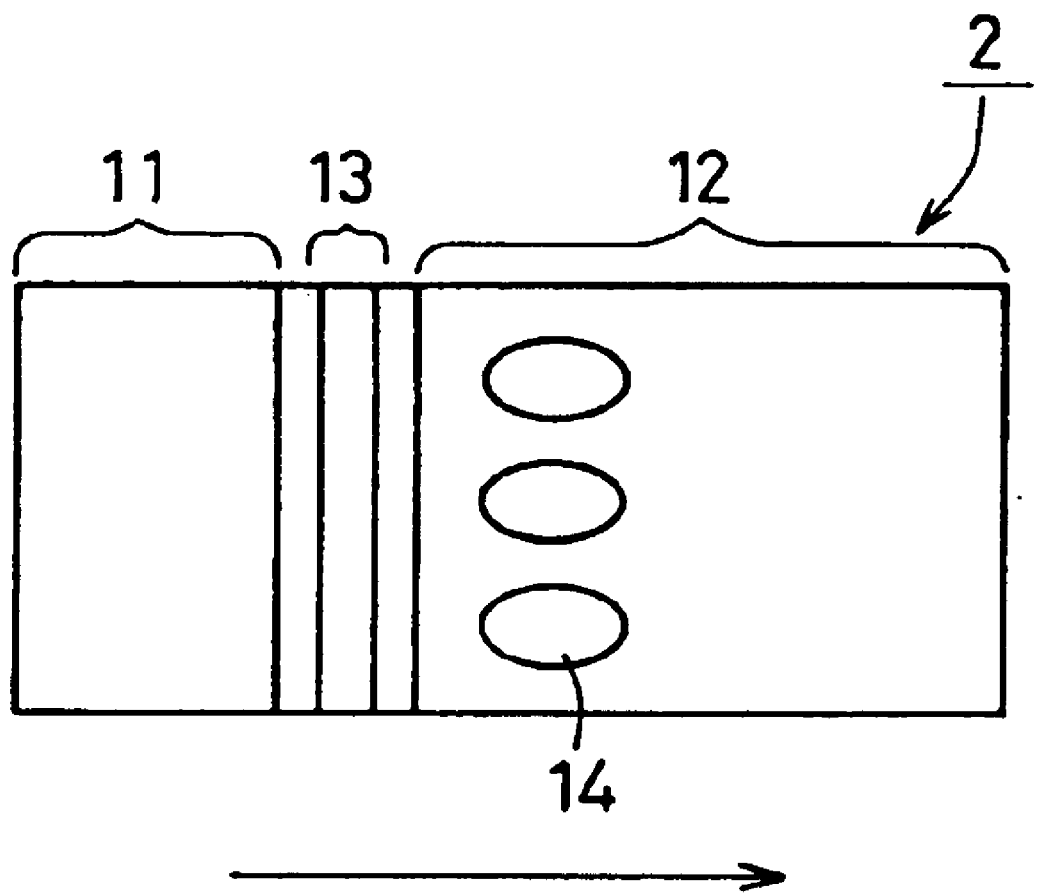
FIG. 2 is a sectional view illustrating another example of a blood testing tool according to the present invention.

As shown in FIG. 2, when reagent portions 14 are provided in a development portion 12 to be parallel to the direction in which blood plasma or blood serum moves, and are provided with reagents, multiple items can be analyzed in a single blood testing tool 2. In this case, in order to prevent reagents for the multiple items from being mixed, it is preferable to provide, for example, boundary layers between the respective reagent portions 14 by impregnation of a hydrophobic resin solution. In FIG. 2, the same parts as those shown in FIG. 1 are indicated with the same numerals.

When no analytical reagent is provided in the development portion, this blood testing tool may be used as a tool for retaining separated blood temporarily or as a tool for long-term preservation of separated blood. In testing the blood, the development portion is taken out from the porous membrane and then blood plasma or blood serum is extracted from the development portion to be tested. In the remote clinical testing system, a blood testing tool retaining specimens including blood cells and blood plasma/serum which are separated is sent to a test institute, and the specimens are tested there. In this application method, blood plasma or blood serum may be retained or preserved in a dried state. In such a case, it is preferable to provide an stabilizing agent such as one described above particularly for the development portion, so as to prevent components in blood plasma or blood serum from deteriorating for example. Alternatively, the whole porous membrane may be provided with a stabilizing agent as described above.

Embodiment A-2

Figure 3:
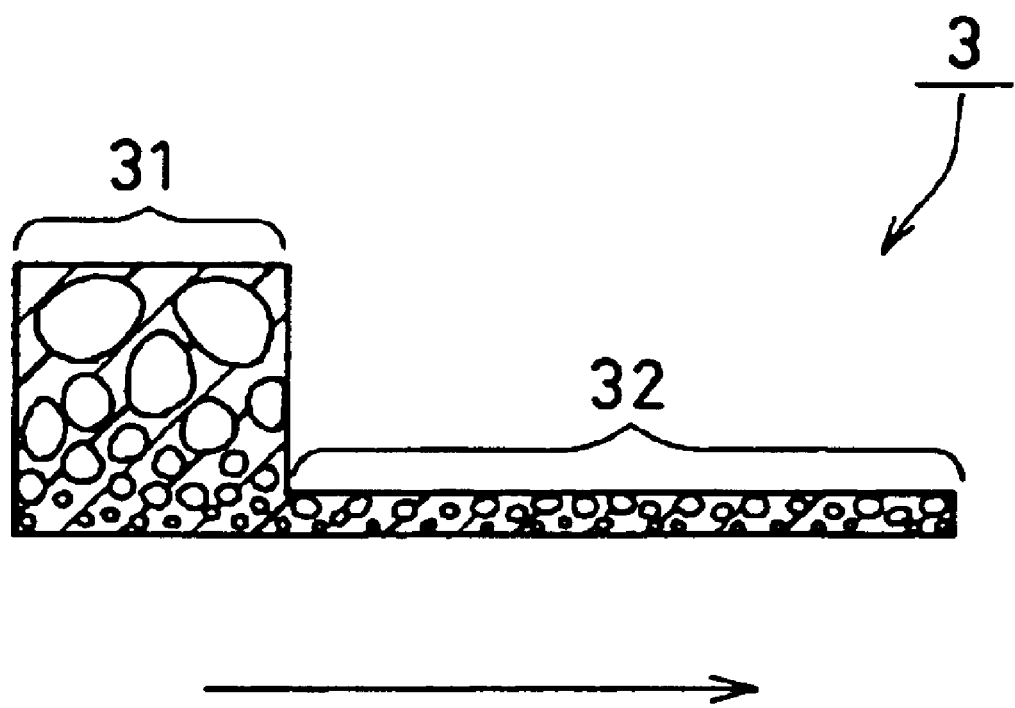
FIG. 3 is a sectional view illustrating a further example of a blood testing tool according to the present invention.

FIG. 3 shows another example of a blood testing tool according to the present invention. As shown in the figure, this blood testing tool 3 is formed of a single asymmetric porous membrane, and the development portion 32 is formed to be thinner than the blood supply portion 31, so that blood cells cannot enter the development portion 32.

In this blood testing tool 3, the thickness of the development portion 32, the maximum pore size and the minimum pore size in the development portion 32, are the same as those of the blood-cell blocking portion in Embodiment A-1. At the boundary between the blood supply portion 31 and the development portion 32, blood cells are blocked and therefore only blood plasma or blood serum is developed. Except for the thickness of and the pore size in the development portion 32, the blood testing tool 3 has the same configuration as that of the blood testing tool according to Example A-1 and can be used in the same manner as in Example A-1.

Such a blood testing tool 3 can be produced as follows. For example, in the region other than the blood supply portion 31 of the porous membrane, a portion with a predetermined thickness on the side with larger pores is cut out with a knife blade or the like.

Embodiment A-3

Figure 4:
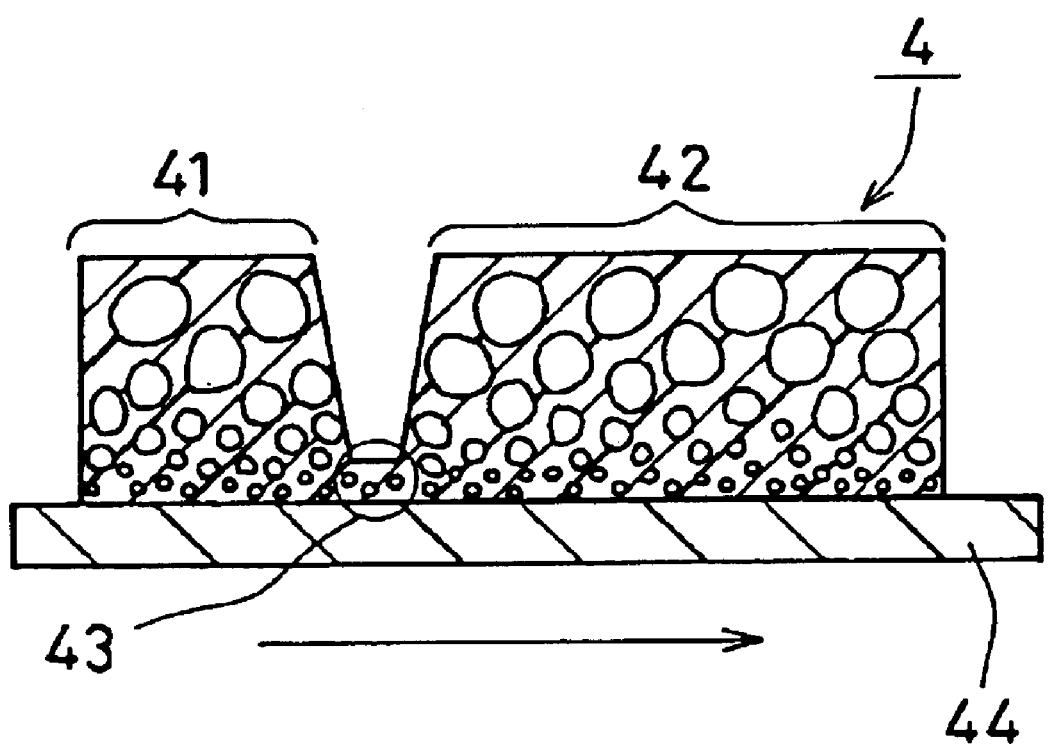
FIG. 4 is a sectional view illustrating still another example of a blood testing tool according to the present invention.

FIG. 4 shows an example of a blood testing tool according to the present invention in which an asymmetric porous membrane is supported by a supporter. As shown in the figure, in this blood testing tool 4, the porous membrane according to Embodiment A-1 is stacked on a supporter 44. In FIG. 4, the same parts as those in FIG. 1 are indicated with the same numerals.

As the material for forming the supporter 44, for example, plastic such as polystyrene, PET, PVC, acrylic resins, ABS, PP, or the like can be used. The material is not limited to only one of them, and two or more of them may be used together.

When the blood testing tool 4 is subjected to measurement from the supporter 44 side directly, for example, by the optical method as described above, it is preferable that the portion of the supporter 44 corresponding to the development portion 42 has optical transparency. In this case, for example, polystyrene, PET, acrylic resins, or the like is preferred as the material.

Furthermore, the supporter may be stacked on an upper surface (the upper surface shown in FIG. 4) of the porous membrane. In this case, preferably, a through hole for supplying blood is provided in a location corresponding to the blood supply portion 41 of the porous membrane.

Embodiment B

Figure 5A:
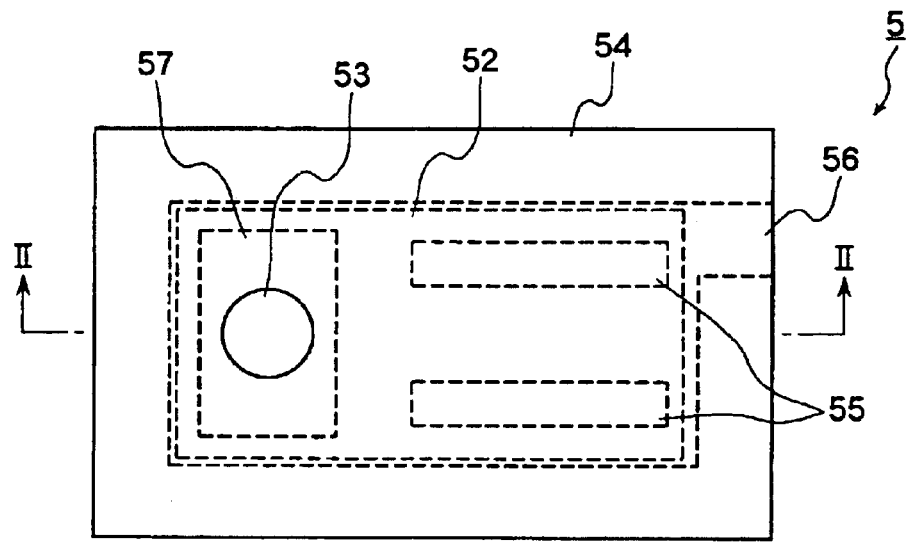
Figure 5B:
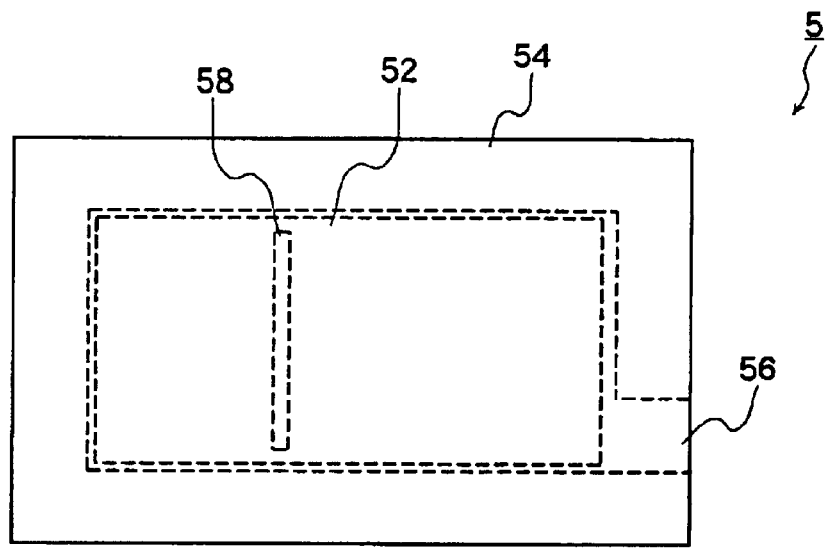
Figure 5C:
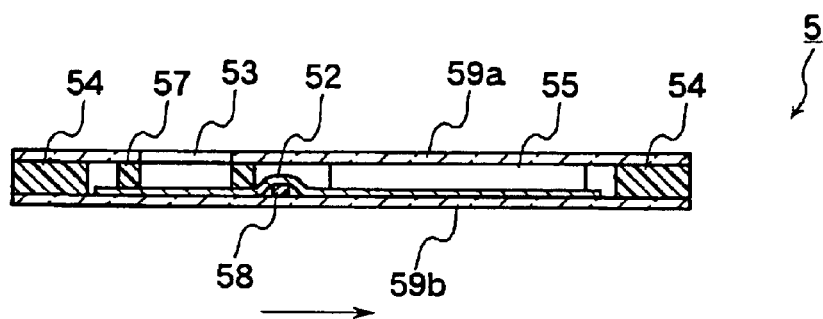
Figure 6:
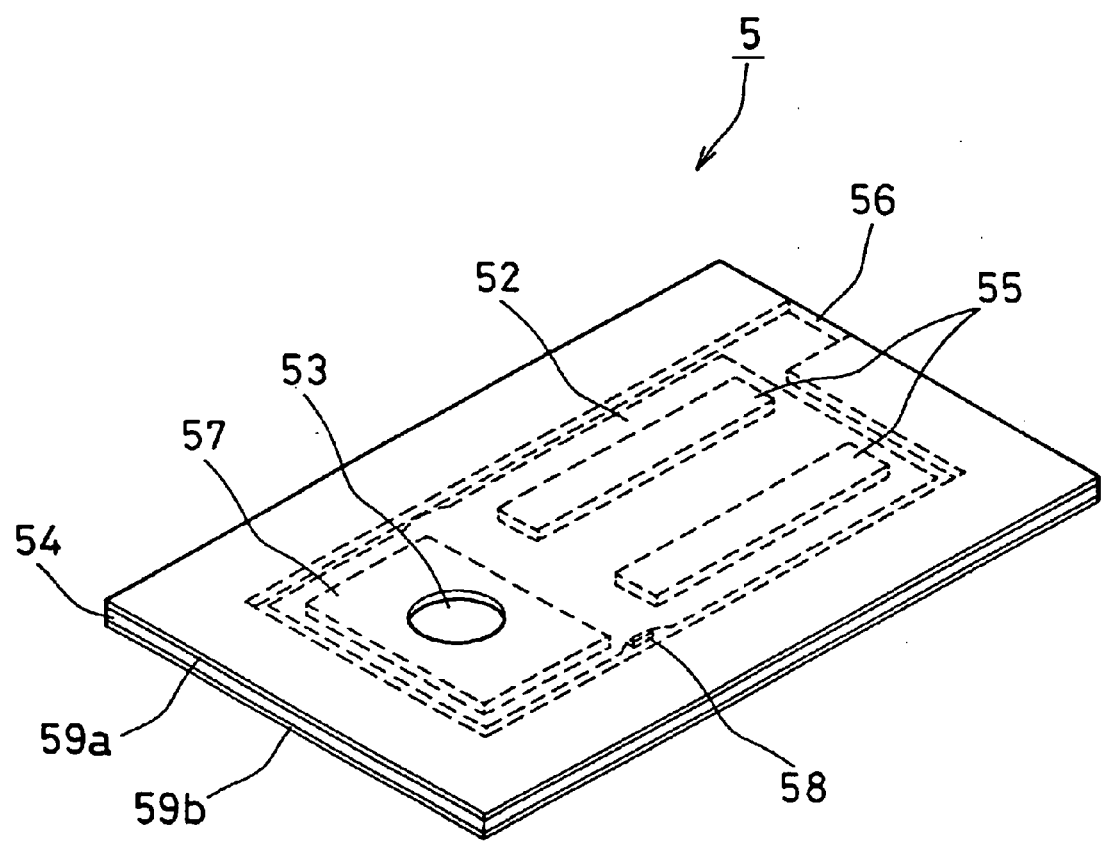
FIG. 6 is a perspective view of the example.

FIGS. 5A, 5B, 5C, and 6 show a first example of the contained-type blood testing tool in which an asymmetric porous membrane is contained in a holder. FIG. 5A is its plan view, FIG. 5B its back side view, and FIG. 5C its sectional view taken in the direction II—II shown in the plan view. FIG. 6 is its perspective view. In the respective figures, the same parts are indicated with the same numerals. The porous membrane to be used and the application method are the same as those in Embodiments A-1 and A-2 as long as no particular indication is provided.

As shown in the figures, in a blood testing tool 5, a spacer 54 is placed around the periphery of a rectangular lower substrate 59b and on the spacer 54, a rectangular upper substrate 59a is placed, thus forming the holder containing a rectangular porous membrane 52 therein. Both the substrates 59a and 59b are transparent. The gap in spacer 54 occurs at one part of the periphery of each substrate so that a space is formed, which serves as an air vent portion 56. On one side of the upper substrate 59a, a hole 53 is formed for supplying blood and the portion of the porous membrane 52 corresponding to the hole 53 is the blood supply portion. On the inner face of the upper substrate 59a, a holding member 57 with a rectangular body is formed around the hole 53 and thus also has a hole communicating with the hole 53, which serves as a blood guide. On the inner face of the lower substrate 59b, a protruding supporter 58 is formed in the transverse direction adjacent to the portion corresponding to the hole 53. The protruding supporter 58 lifts a part of the porous membrane 52, whereby a space between the inner face (inner wall) of the lower substrate 59b and the porous membrane 52 is formed. In the porous membrane 52, the portion corresponding to the space is a boundary portion (for instance, a blood-cell blocking portion), and the opposite side to the blood supply portion with respect to the boundary portion is a development portion. In the region of the development portion, two holding members 55 with rectangular bodies formed on the inner face of the upper substrate 59a, fix both ends of the development portion along its longitudinal direction to the inner wall of the lower substrate 59b. In this way, preferably, the holding members do not hold the whole development portion of the porous membrane but only its periphery.

In this blood testing tool 5, when blood is dropped on the blood supply portion of the porous membrane 52 through the hole 53, the blood moves inside the porous membrane 52 in the surface direction by a capillary phenomenon. Then, blood cells are blocked in the boundary portion between the blood supply portion and the development portion and thus only blood plasma or blood serum develops in the development portion. In FIG. 5C, the arrow indicates the direction in which the blood moves. Since this blood testing tool 5 has an air vent 56, the blood develops quickly. The blood also moves in the thickness direction of the porous membrane 52 and comes into contact with the inner face of the lower substrate 59b. However, since a space with a size preventing the capillary phenomenon from occurring is formed between the boundary portion (the blood-cell blocking portion) of the porous membrane 52 and the inner face of the lower substrate 59b, non-separated blood does not permeate between the porous membrane 52 and the inner face of the lower substrate 59b to move to the development portion of the porous membrane 52.

The size of the blood testing tool 5 can be determined according to, for example, the size of the porous membrane to be contained or the like. The blood testing tool 5 has, for instance, an overall size of 5 mm×30 mm to 50 mm×80 mm and an overall thickness of 0.5 to 10 mm. The hole 53 has a diameter of 3.0 to 20 mm, the holding members 55 have a height of 0.1 to 0.2 mm, the holding member 57 around the hole 53 has a height of 0.1 to 5.0 mm, and the supporter 58 on the lower substrate 59b has a height of 0.05 to 3.0 mm. Preferably, the blood testing tool 5 has an overall size of 5 mm×40 mm to 40 mm×70 mm and an overall thickness of 0.5 to 5.0 mm, the hole 53 has a diameter of 4.0 to 10 mm, the holding members 55 have a height of 0.3 to 1.0 mm, the holding member 57 around the hole 53 has a height of 0.3 to 2.0 mm, and the supporter 58 on the lower substrate 59b has a height of 0.2 to 1.0 mm. More preferably, the blood testing tool 5 has an overall size of 10 mm×50 mm to 30 mm×60 mm and an overall thickness of 1.0 to 3.0 mm, the hole 53 has a diameter of 5.0 to 7.0 mm, the holding members 55 have a height of 0.4 to 0.8 mm, the holding member 57 around the hole 53 has a height of 0.5 to 1.0 mm, and the supporter 58 on the lower substrate 59b has a height of 0.3 to 0.7 mm. The size, thickness, and the like of the porous membrane are not particularly limited, but may be the same as those in Embodiment A-1.

In this blood testing tool, the material used for forming the holder is chosen as described above.

Embodiment C

Figure 7:
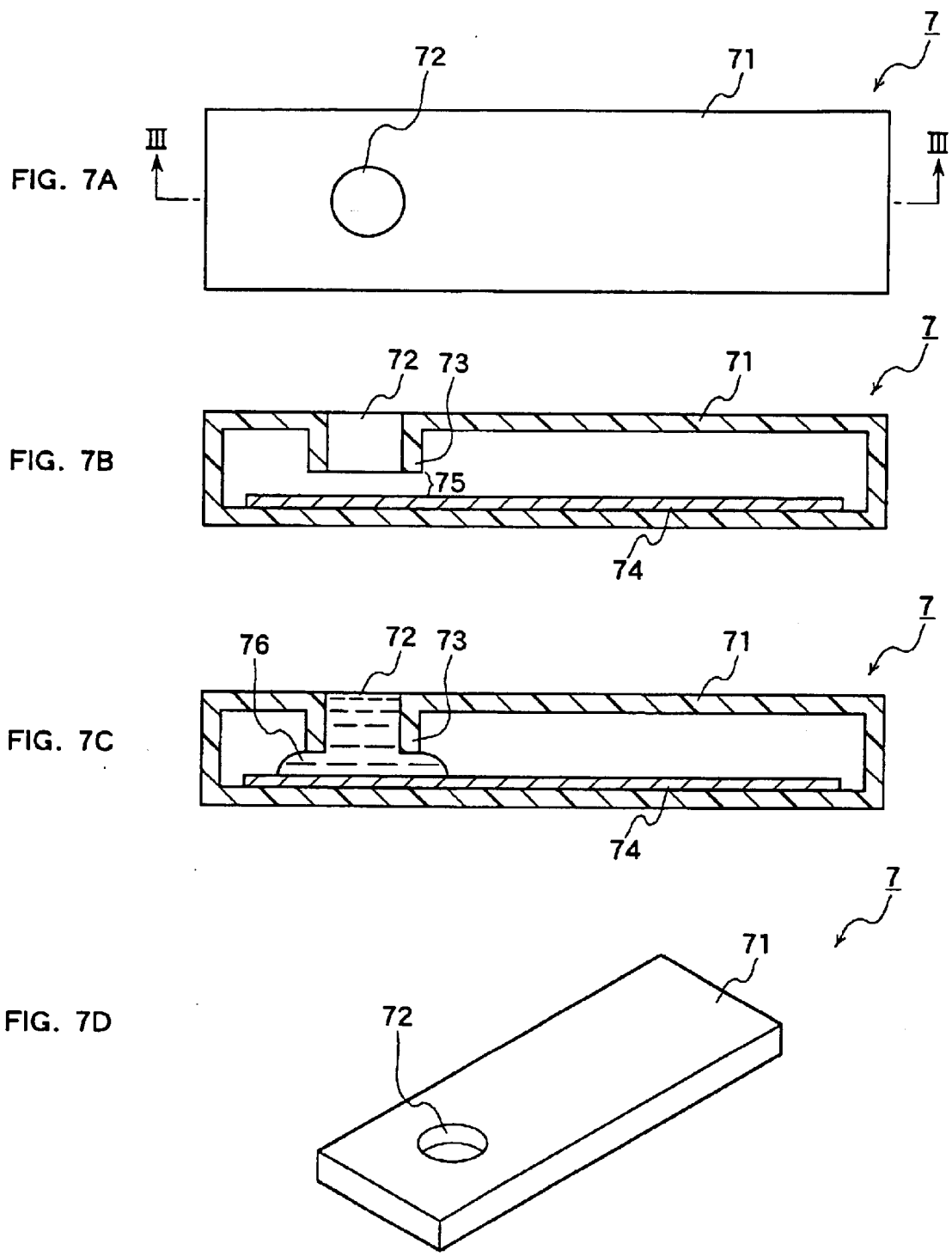

FIGS. 7A, 7B, 7C, and 7D show a second example of a blood testing tool, wherein FIG. 7A is its plan view, FIGS. 7B and 7C are its sectional views taken in the direction III—III shown in the plan view, and FIG. 7D is its perspective view. In the figures, the same parts are indicated with the same numerals. The asymmetric porous membrane to be used and application methods are the same as in Examples A-1 and A-2 as long as no particular indication is provided.

As shown in the figures, in this blood testing tool 7, an asymmetric porous membrane 74 is contained in a holder 71 with a flat rectangular body. A hole 72 is formed on a side (on the left side in the figures) of one end of the upper surface of the holder 71 with respect to its center. An annular protrusion 73 is formed on the inner wall of the holder 71 to surround the hole 72. The hole 72 and the annular inner space of the annular protrusion 73 together form a blood guide hole. In the porous membrane 74, the portion corresponding to the blood guide hole is the blood supply portion. In the figures, the portion to the right of the blood supply portion is the development portion. The end of the annular protrusion is the lower end of the blood guide hole, and between the lower end and the blood supply portion of the porous membrane 74, a space 75 with a predetermined height is formed. The height of this space 75 is as described above.

In this blood testing tool 7, when blood is dropped through the hole 72, blood 76 is retained temporarily inside the blood guide hole (in the inner portions of the hole 72 and the annular protrusion 73) and in the space 75. In this state, the volume of the blood retained inside the blood guide hole and in the space 75 is constant, and therefore the blood can be supplied to the porous membrane 74 quantitatively. A predetermined space is provided between the porous membrane 74 and the inner wall of the holder 71, thus preventing blood from penetrating between them by the capillary phenomenon. After that, the blood moves inside the porous membrane 74 in the surface direction. In the boundary portion (for instance, a blood-cell blocking portion) between the blood supply portion and the development portion, blood cells are blocked, and therefore only blood plasma or blood serum develops in the development portion of the porous membrane 74 by the capillary phenomenon (from the left to the right in the figures).

The size of the blood testing tool 7 in the present embodiment is not particularly limited. Preferably, the holder has an outer overall length of 30 to 50 mm, an inner overall length of 25 to 45 mm, an outer width of 10 to 30 mm, an inner width of 5 to 25 mm, an outer thickness of 1 to 3 mm, and an inner thickness of 0.5 to 2.5 mm. Preferably, the blood guide hole has a diameter of 3 to 10 mm and a length of 0.1 to 1 mm, and the annular protrusion has a height of 0.1 to 1 mm and a width of 0.1 to 1 mm. The size of the porous membrane 74 is the same as described above. The size, thickness, and the like of the porous membrane are not particularly limited, but may be the same as those, for example, in Example A-1.

EXAMPLE

Example 1

A strip-shaped asymmetric porous membrane (made of polysulfone, with a length of 35 mm, a width of 16 mm, a thickness of 320 $\mu$m, a maximum pore size of 50 to 100 $\mu$m, and a minimum pore size of 5 to 10 $\mu$m) was treated to be provided with hydrophilicity by being dipped in a 20 wt % glycine solution, was dipped in a 30 wt % sucrose solution, and then was dried. At a location 12 mm along the length of the porous membrane with respect to one of its ends, a disc roller was pressed against and rolled on the portion to form a groove (with a minimum width of 0.1 mm, a maximum width of 1 mm, and a depth of 150 to 250 $\mu$m) in its width direction, thus producing a blood testing tool such as shown in FIG. 1. In this blood testing tool, the blood supply portion has a length of 11 mm and the development portion has a length of 23 mm.

On the center portion of the blood supply portion, 100 $\mu$l whole blood of a healthy subject was dropped, and blood serum was allowed to develop sufficiently in the development portion, which was then dried. The development portion was cut out from the blood testing tool and further was cut to be in a strip shape. This cut piece was put into a test tube (with a volume of 500 $\mu$l), to which a 150 $\mu$l PBS solution (Phosphate-buffered saline, with pH 7.4, the same is true for the following description) was added as an extractant. This was left at room temperature for 20 minutes and then subjected to centrifugation, thus obtaining a supernatant, which was used as a serum sample solution.

In the same manner as described above, a total of 20 serum sample solutions were prepared from 20 specimens and respective components in the serum sample solutions were subjected to the measurements described below. As a control, blood plasma was used. In this case, whole blood of the same healthy subject was collected with a heparin collecting vessel and then was subjected to centrifugation (3000 rpm, 10 minutes), in order to prepare the blood plasma.

Amounts of the respective components in the respective serum sample solutions obtained in the example and the blood plasma sample solution as a control were measured using the following commercially available kits according to their application methods. In various measurements, purified water was used as a blank.

1. Urea Nitrogen (BUN)
   Product Name: Urea Nitrogen II-HA Test Wako (7070: Wako Pure Chemical Industries, Ltd.)
2. Triglyceride (TG)
   Product Name: Triglyceride E-HA Test Wako (Wako Pure Chemical Industries, Ltd.)
3. Glucose (Glc)
   Product Name: Glucose II-HA Test Wako (Wako Pure Chemical Industries, Ltd.)
4. Total Cholesterol (T-Cho)
   Product Name: Determiner L TCII (Kyowa Medex Co., Ltd.)
5. Glutamic-Oxaloacetic Transaminase (GOT)
   Product Name: Transaminase HR-II (GOT-7070: Wako Pure Chemical Industries, Ltd.)
6. Glutamic-Pyruvic Transaminase (GPT)
   Product Name: Transaminase HR-II (GPT-7070: Wako Pure Chemical Industries, Ltd.)
7. $\gamma$-Glutamyl Transpeptidase ($\gamma$-GTP)
   Product Name: $\gamma$-GTP J-HA Test Wako (Wako Pure Chemical Industries, Ltd.)
8. Creatine Kinase (CPK)
   Product Name: CK E-HA Test Wako (Wako Pure Chemical Industries, Ltd.)

Figure 8:
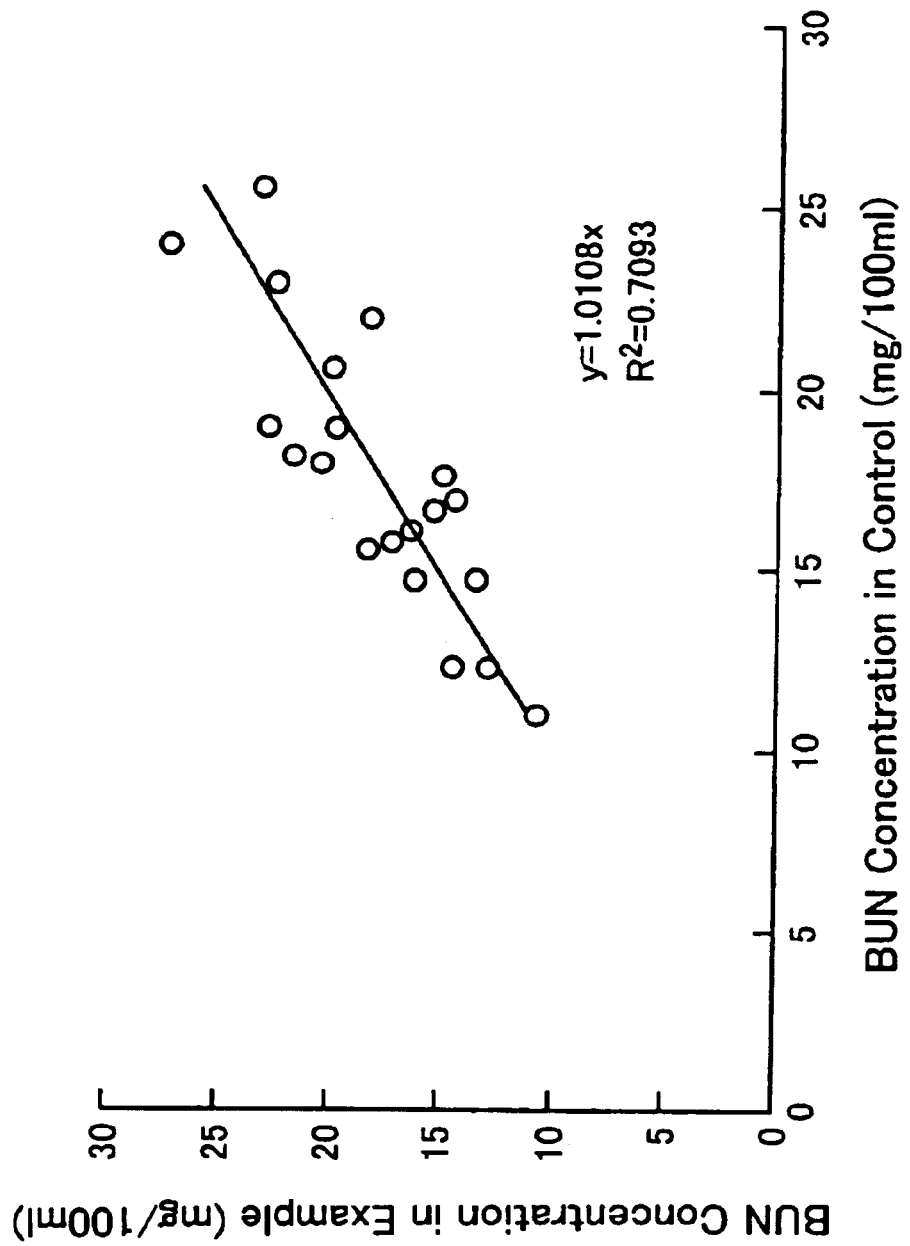
FIG. 8 is a graph showing an amount of BUN in collected blood serum in an example of the present invention.
Figure 9:
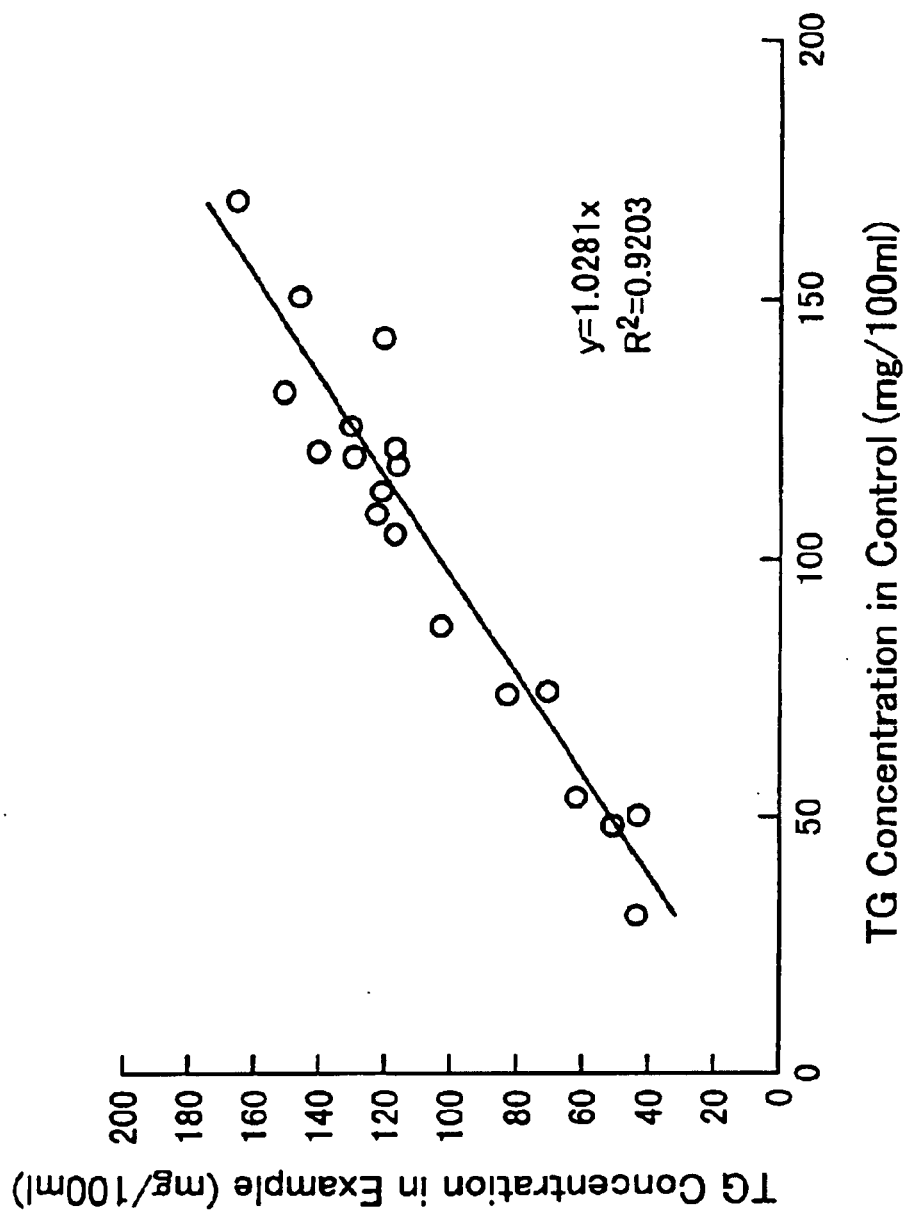
FIG. 9 is a graph showing an amount of TG in the collected blood serum in the example of the present invention.
Figure 10:
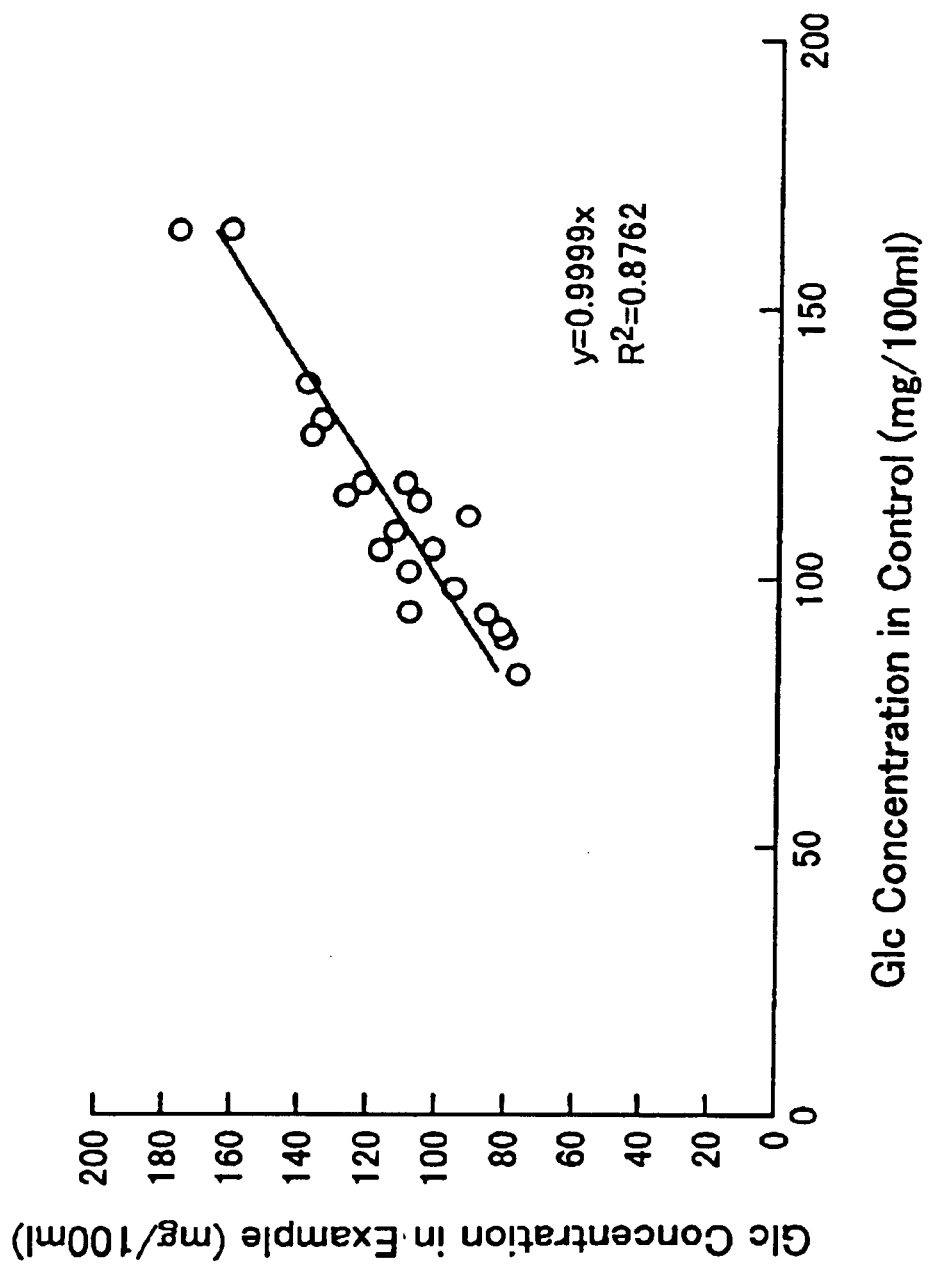
FIG. 10 is a graph showing an amount of Glc in the collected blood serum in the example of the present invention.
Figure 11:
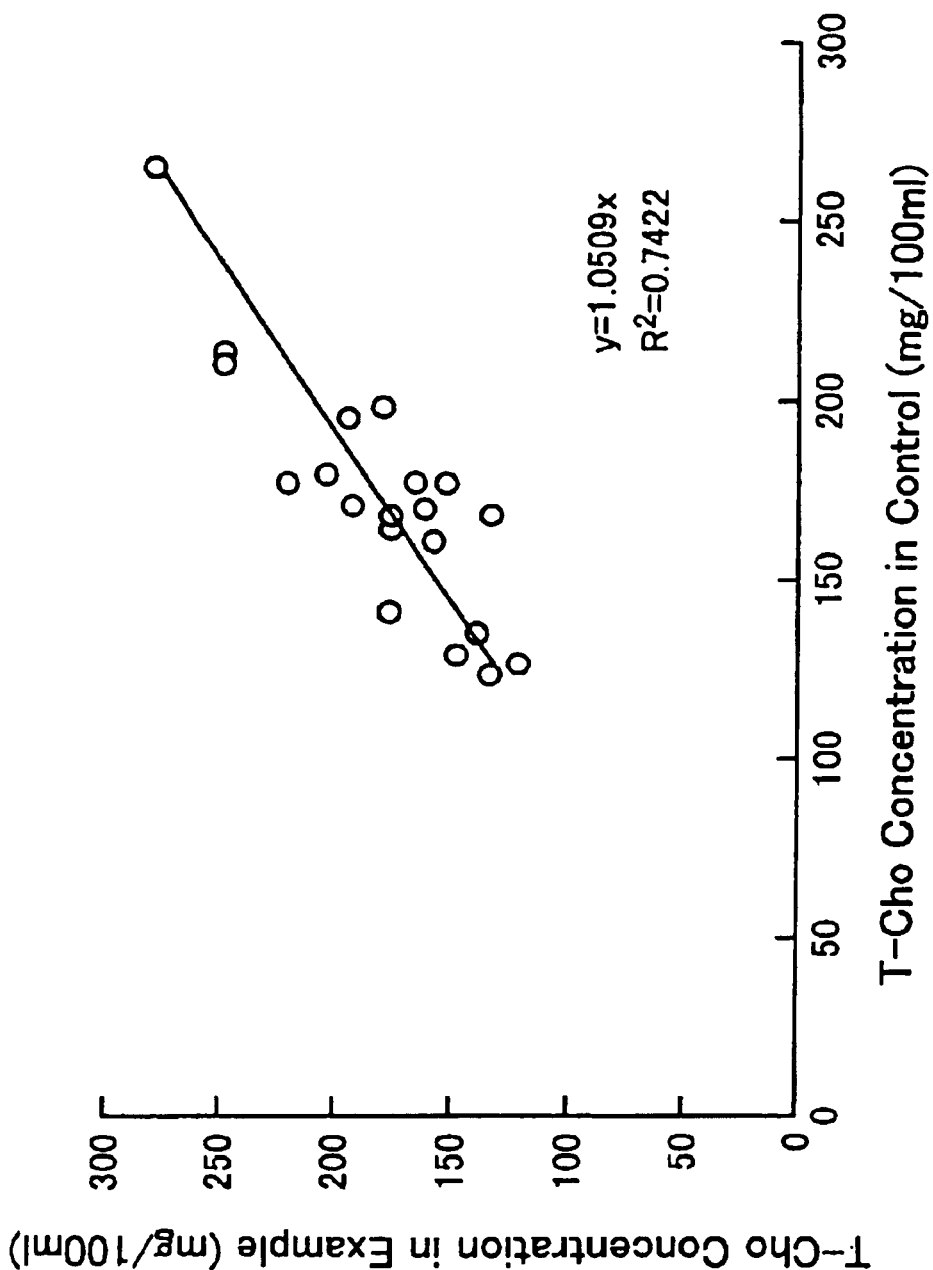
FIG. 11 is a graph showing an amount of T-Cho in the collected blood serum in the example of the present invention.
Figure 12:
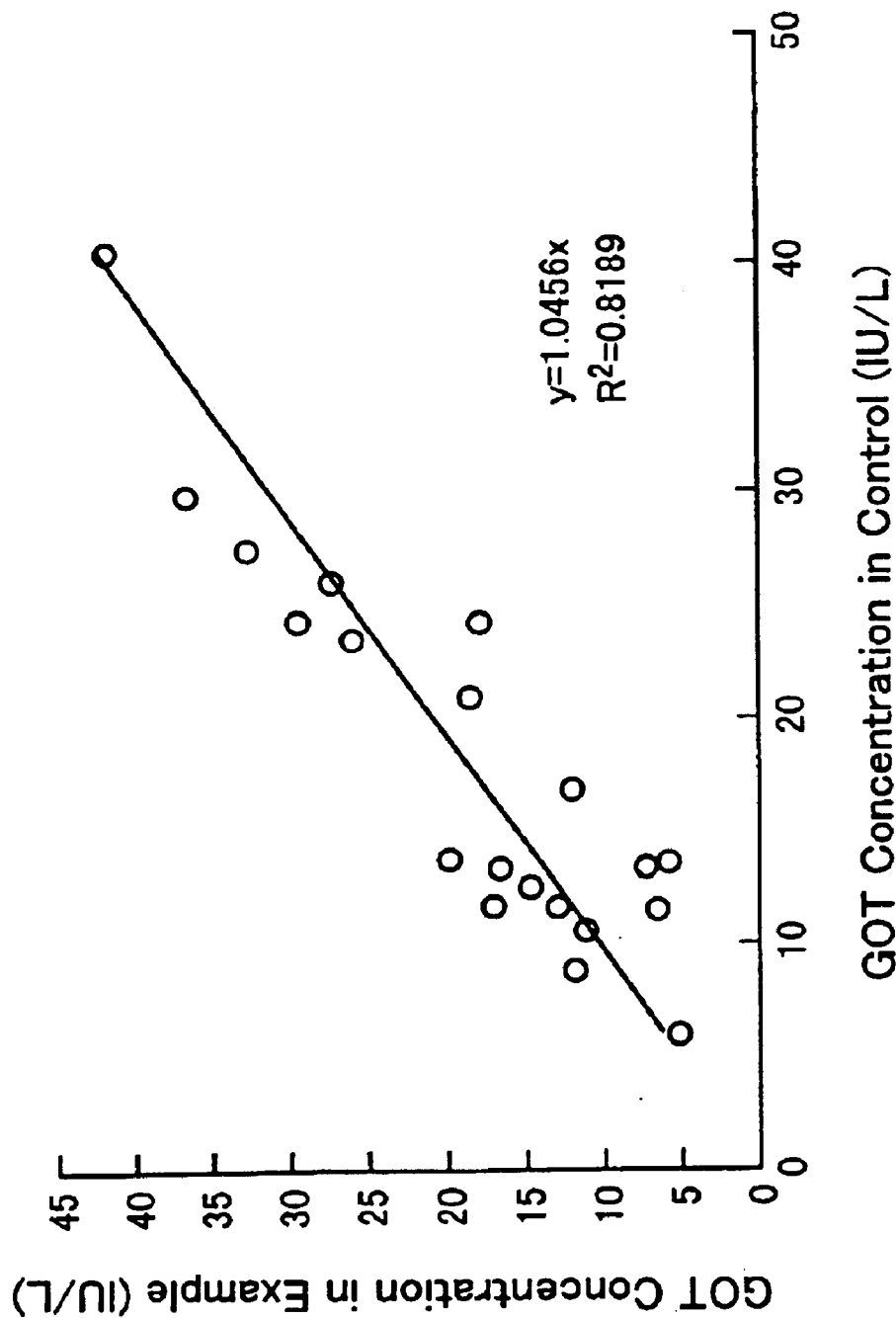
FIG. 12 is a graph showing an amount of GOT in the collected blood serum in the example of the present invention.
Figure 13:
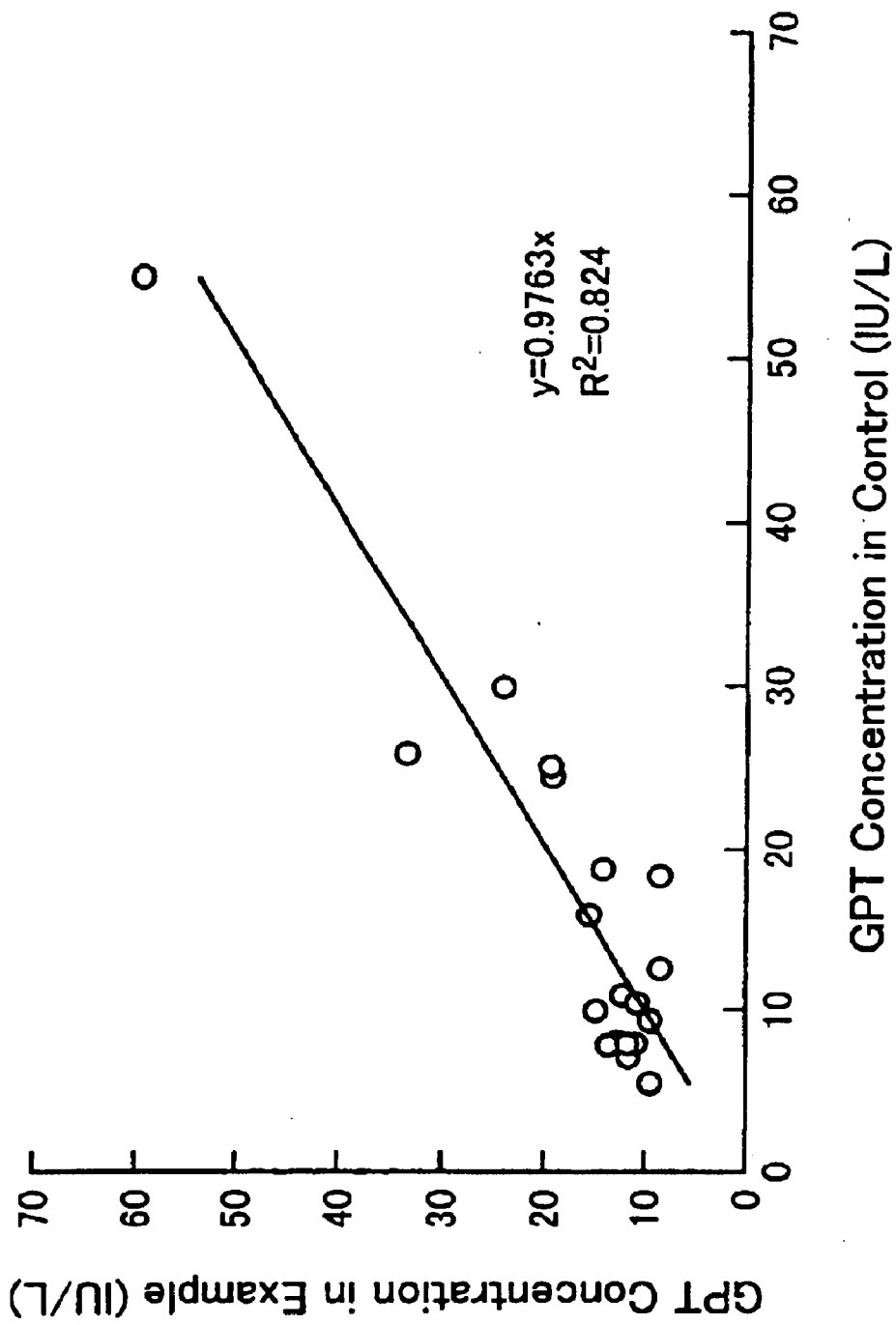
FIG. 13 is a graph showing an amount of GPT in the collected blood serum in the example of the present invention.
Figure 14:
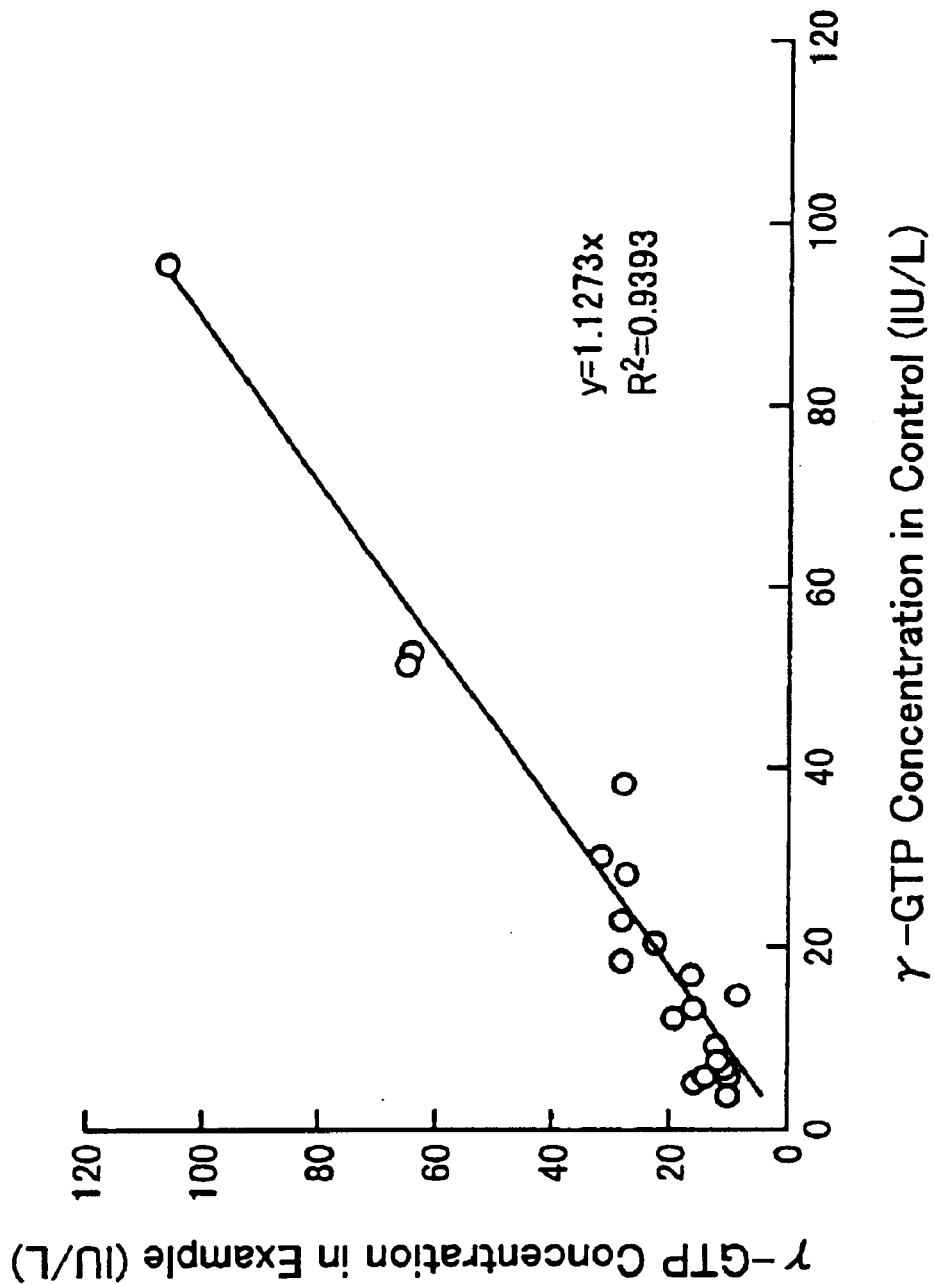
FIG. 14 is a graph showing an amount of γ-GTP in the collected blood serum in the example of the present invention.
Figure 15:
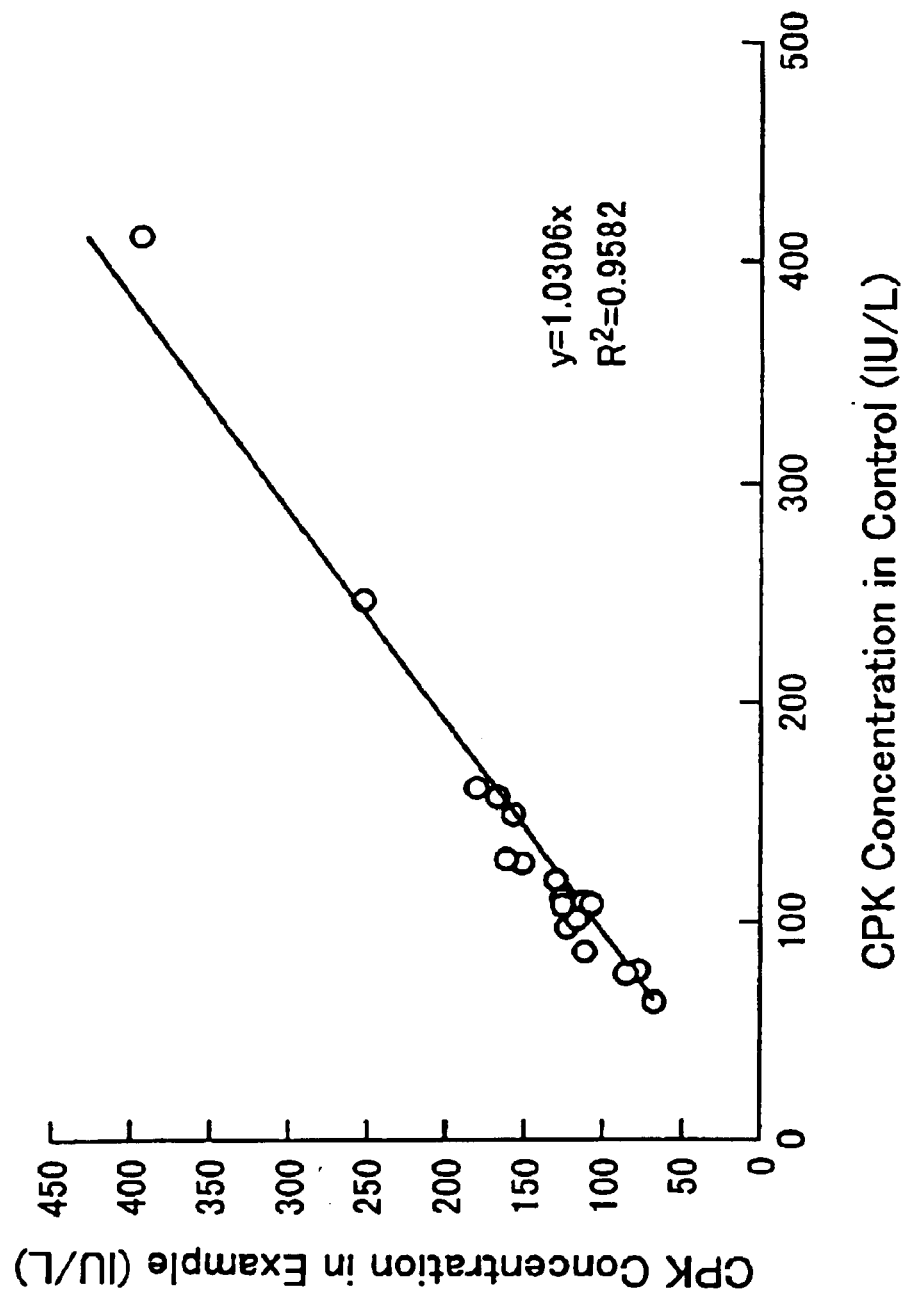
FIG. 15 is a graph showing an amount of CPK in the collected blood serum in the example of the present invention.

FIGS. 8 to 15 show the results. These figures show graphs indicating the relationships between the amounts of the components in the serum samples prepared using the blood testing tool according to the present invention (Example) and the amounts of the components in the control. FIG. 8 shows the amount (concentration) of BUN, FIG. 9 that of TG, FIG. 10 that of Glc, FIG. 11 that of T-Cho, FIG. 12 that of GOT, FIG. 13 that of GPT, 14 that of $\gamma$-GTP, and FIG. 15 that of CPK.

As shown in the figures, the same amounts of the components as those of the blood plasma (control) prepared by centrifugation were obtained from the serum sample prepared using the blood testing tool according to the present invention. The amounts of the blood plasma (control) and the serum sample had high correlativity to each other. This means that when the blood serum is collected using the blood testing tool of the present invention, the measurements of the components in the blood serum are highly reliable. In addition, no red color derived from hemoglobin was found in the development portion of the blood testing tool, thus confirming that blood cells were separated adequately.

Example 2

The same blood testing tool as in Example 1 was produced. Then, 100 $\mu$l whole blood (with 40% hematocrit (Ht)) of a healthy subject, which was collected using a heparin blood-collecting vessel, was dropped on the center portion of a blood supply portion of the blood testing tool. In the development portion of the blood testing tool, the blood plasma was allowed to develop sufficiently, and this was then dried. Afterwards, an extraction operation was conducted as in Example 1 and a supernatant thus obtained and used as a blood plasma sample solution. In the same manner, a total of 20 blood testing tools were produced and blood plasma sample solutions from the same blood were prepared.

Comparative Example 1

The same porous membrane (with a length of 14 mm and a width of 14 mm) as that used in Example 1 was stacked on a cellulose film (with a length of 14 mm, a width of 14 mm, and a thickness of 550 μm) to be a development portion without being processed (without being provided with a groove), thus producing a stacked-type blood testing tool. The cellulose film was prepared by being dipped in a 30 wt % sucrose solution and then being dried. The porous membrane was stacked on the cellulose film with the one side with smaller pores facing the cellulose film.

Then, the same whole blood as in Example 2 was dropped on the surface of the porous membrane of the blood testing tool, and blood plasma was allowed to develop in the cellulose film, which then was dried. After that, the porous membrane and the cellulose film were separated and the cellulose film was cut to be in a strip shape. Using this, the extraction operation was carried out under the same conditions as in Example 1. A supernatant thus obtained was used as a blood plasma sample solution. In the same manner, a total of 20 stacked-type blood testing tools were produced and blood plasma sample solutions from the same blood were prepared.

Amounts of collected blood plasma and of hemoglobin (Hb) in the respective blood plasma sample solutions according to Example 2 and Comparative Example 1 were measured by the following methods. The results are shown in Tables 1 and 2.

Measurement of Amount of Collected Blood Plasma

With respect to the respective blood plasma sample solutions according to Example 2 and Comparative Example 1, the amount of total protein was measured using an autoanalyzer (BM-8 manufactured by Nippon Electronic Co., Ltd.). Then, based on a theoretical value of the blood plasma amount in 100 μl whole blood and the amount of total protein in the blood plasma, amounts of collected blood plasma were determined from the measurement values of the total protein in Example 2 and Comparative Example 1. The theoretical value of the blood plasma amount was assumed to be 60 μl since Ht in the whole blood was 40%. The reference value of the amount of total protein in the blood plasma was a measurement value measured using the autoanalyzer with respect to the blood plasma obtained by centrifugation of the same whole blood. The collection rate of the blood plasma is a relative value (%) with respect to 100% of the theoretical value of the blood plasma amount.

Measurement of Hb

With respect to a Hb solution with a known concentration, its absorbance in the case of using a wavelength of 410 nm was measured to prepare a calibration curve. Then, the absorbance in the wavelength of 410 nm of the respective blood plasma sample solutions was measured. From the absorbance and the calibration curve, the Hb concentration was determined.

TABLE 1

|  | Number of Samples | Amount of Collected Blood Plasma (μl) | Collection Rate of Blood Plasma (%) |
| --- | --- | --- | --- |
| Example 2 | 20 | 39–46 (Average 42) | 65–77 (Average 70) |
| Comparative Example 1 | 20 | 11–41 (Average 17) | 18–68 (Average 28) |

TABLE 2

|  | Number of Samples | Hb Concentration (μg/μl) |
| --- | --- | --- |
| Example 2 | 20 | 0–170 (Average 40) |
| Comparative Example 1 | 20 | 70–720 (Average 220) |

As shown in Table 1, when using the blood testing tool according to Example 2, blood plasma was collected with at least twice the yield compared to that collected using the blood testing tool according to Comparative Example 1. Furthermore, the blood cells that reached the development portion and hemolysis of them were checked by the measurement of the Hb concentration in the blood plasma samples. As a result, as shown in Table 2, the blood testing tool of the example hardly allowed blood cells to move to the development portion and also prevented hemolysis from occurring. Thus, it was confirmed that according to the blood testing tool of Example 2, blood plasma was collected with a high yield, blood cells were separated adequately, which otherwise hinder the measurements of various components, and hemolysis also was prevented.

As described above, according to the blood testing tool of the present invention, blood plasma or blood serum can be collected with a high yield and blood cells can be separated adequately. Therefore, even with a small amount of blood sample, a sufficient amount of blood plasma or blood serum can be collected. Therefore, the blood testing tool of the present invention is useful in fields such as clinical medicine, for example, particularly in a remote clinical testing system in which the amount of collected blood is limited.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A blood testing tool, comprising an asymmetric porous membrane with a pore size distribution in which an average pore size varies so that it is reduced continuously or discontinuously in a thickness direction, wherein the asymmetric porous membrane includes a blood supply portion, a development portion, and a blood-cell blocking portion formed between the blood supply portion and the development portion, pores in the blood-cell blocking portion include only pores through which blood cells cannot pass, the arrangement being such that when blood is supplied to the blood supply portion at a side having larger pores, the blood moves in a direction substantially parallel to a surface of the asymmetric porous membrane by capillary action, and when the blood reaches the blood-cell blocking portion, the movement of blood cells in a direction substantially parallel to the surface is blocked, such that only blood plasma or blood serum moves into the development portion.

2. The blood testing tool according to claim 1, further comprising a groove formed between the blood supply portion and the development portion, wherein a portion between a bottom of the groove and a part of a surface of the asymmetric porous membrane corresponding to the bottom is the blood-cell blocking portion.

3. The blood testing tool according to claim 1 or 2, wherein pores in the development portion include only pores through which blood cells cannot pass.

4. The blood testing tool according to claim 1, wherein the pores in the blood-cell blocking portion have a pore size in a range of 1 to 50 μm.

5. The blood testing tool according to claim 1, wherein in the asymmetric porous membrane, the maximum pore size is in a range of 30 to 300 μm and the minimum pore size is in a range of 1 to 30 μm.

6. The blood testing tool according to claim 1, wherein the asymmetric porous membrane has a single layer structure.

7. The blood testing tool according to claim 1, wherein the asymmetric porous membrane is supported by a supporter.

8. The blood testing tool according to claim 1, wherein the asymmetric porous membrane is formed from at least one resin selected from a group consisting of polysulfone, polyamide, polyimide, polycarbonate, polystyrene, and polyaryl hydrazide.

9. The blood testing tool according to claim 1, wherein the asymmetric porous membrane is treated to be provided with hydrophilicity.

10. The blood testing tool according to claim 1, wherein the development portion comprises a stabilizing agent for maintaining stability of components in the blood plasma or the blood serum.

11. The blood testing tool according to claim 1, wherein the development portion comprises an analytical reagent.

12. The blood testing tool according to claim 2, wherein the groove is formed by compression of a part of the asymmetric porous membrane.

13. The blood testing tool according to claim 2, wherein the groove is formed by cutting out of a part of the asymmetric porous membrane.

14. The blood testing tool according to claim 1, further comprising a holder,
wherein the holder contains the asymmetric porous membrane, and a space with a size preventing a capillary phenomenon from occurring is formed between an inner wall of the holder and a portion between the development portion and the blood supply portion.

15. The blood testing tool according to claim 14, further comprising a protruding supporter formed inside the holder, wherein the protruding supporter lifts the portion between the development portion and the blood supply portion, thus forming the space.

16. The blood testing tool according to claim 15, further comprising a protruding holding portion formed inside the holder on an opposite side to the side on which the protruding supporter is formed, wherein the holding portion fixes the development portion to the inner wall of the holder on the side on which the protruding supporter is formed.

17. The blood testing tool according to claim 14, wherein the portion between the blood supply portion and the development portion is the blood-cell blocking portion.

18. The blood testing tool according to claim 14, wherein the space has a height in a range of 0.05 to 3 mm.

19. The blood testing tool according to claim 1, further comprising a holder,
wherein the holder contains the asymmetric porous membrane and has a blood guide hole at a position corresponding to the blood supply portion, a predetermined space is provided between a lower end of the blood guide hole and the blood supply portion, and blood is retained in the space quantitatively by surface tension of the blood.

20. The blood testing tool according to claim 19, wherein the holder has a hole and an annular protrusion is formed on an inner wall of the holder so as to surround the hole, so that the blood guide hole is formed by the hole and a space inside the annular protrusion, and an end of the annular protrusion is the lower end of the blood guide hole.

21. The blood testing tool according to claim 19, wherein the space has a height in a range of 10 to 3,000 μm.

22. The blood testing tool according to claim 14 or 19, wherein a part of the holder corresponding to the development portion is transparent.

23. The blood testing tool according to claim 14 or 19, wherein a slit is formed at a part of the holder corresponding to the development portion.

24. The blood testing tool according to claim 19, wherein a space with a size preventing a capillary phenomenon from occurring is formed between an inner wall of the holder and a portion between the development portion and the blood supply portion.

25. The blood testing tool according to claim 1, wherein the development portion and the blood supply portion are adjacent to each other in a direction substantially parallel to the surface of the asymmetric porous membrane.

26. The blood testing tool according to claim 2, wherein the groove is formed by removing portions of the membrane having a pore size through which blood cells can pass.

* * * * *